United States Patent [19]
Schmidt et al.

[11] Patent Number: 5,838,244
[45] Date of Patent: Nov. 17, 1998

[54] INTERFACE PRESSURE MEASUREMENT DEVICE

[75] Inventors: Robert N. Schmidt, Cleveland; Steven P. Hendrix, Sagamore Hills, both of Ohio

[73] Assignee: Cleveland Medical Devices Inc., Cleveland, Ohio

[21] Appl. No.: 727,240

[22] Filed: Oct. 8, 1996

[51] Int. Cl.$^6$ .................................................. G08B 21/00

[52] U.S. Cl. .................. 340/635; 340/626; 128/774; 128/782; 73/172

[58] Field of Search .................. 340/635, 626; 128/774, 782; 73/172

[56] References Cited

U.S. PATENT DOCUMENTS

| | | | |
|---|---|---|---|
| 4,554,930 | 11/1985 | Kress | 128/774 |
| 4,794,935 | 1/1989 | Viesturs | 128/774 |
| 4,869,265 | 9/1989 | McEwen | 128/774 |
| 5,224,469 | 7/1993 | Mocny | 128/55 |
| 5,253,656 | 10/1993 | Rincoe et al. | 128/782 |

*Primary Examiner*—Edward Lefkowitz
*Attorney, Agent, or Firm*—John H. Vynalek; Robert N. Schmidt

[57] ABSTRACT

An interface pressure measurement device, comprising a sensor comprising two sensor sheets formed from thin flexible plastic material, each sensor sheet has a sensor area having flexible conductive ink printed thereon comprising a conductive surface with an electrical lead such that when the sensor sheets touch, an electrical contact is present forming a sensor switch, and the sensor also has sensor tubing. A digital device is connected to the sensor by the sensor tubing. The digital device comprises an enclosure, a push button, pressure transducer, signal conditioning, microcontroller with processor, analog-to-digital converter, memory, clock, display, buzzer and battery/power supply wherein the processor interrupts the battery/power supply current flow to shut off the digital device after a preset time. An inflator bulb having inflator tubing is connected to the digital device by the inflator tubing such that the inflator bulb is used to manually pump air through the digital device to the sensor whereby the pressure from the air in the sensor between the sensor sheets is sensed by the pressure transducer. When the microcontroller senses the opening of the sensor switch, the microcontroller through the processor transmits a signal to the display to provide a visual indication corresponding to the pressure in the sensor and transmits a signal to the buzzer to provide an audible tone.

15 Claims, 2 Drawing Sheets

INTERFACE PRESSURE MEASUREMENT DEVICE

BACKGROUND OF THE INVENTION

The present invention relates, generally, to instruments for measuring pressure and, specifically, to instruments for measuring pressure exerted by support surfaces on a body or by bandages applied to a body.

The measurement of interface pressure between a body and a support surface is frequently important. For patients who are confined to a bed or a wheelchair, it is important to keep the skin/support surface interface pressure to an acceptable level. Decubitus ulcers, commonly referred to as pressure sores, can result from excessive interface pressures for prolonged periods of time. By measuring the interface pressure, corrective support surfaces can be prescribed to reduce the interface pressure, thus reducing or eliminating the formation of pressure sores.

Another use for the interface pressure measurement device is to measure bandage wrapping pressures. Pressure bandages are frequently applied to legs of patients with venous ulcers to speed healing. Wrapping these pressure bandages too loose does no good. Wrapping them too tight cuts off circulation and can further damage the tissue. The interface pressure measurement devices provides a means to evaluate the tightness of the wrap.

Other similar devices have been made in the past. U.S. Pat. No. 4,794,935 to Viesturs discloses an instrument for measuring pressure. That instrument was complex in that it required the user to simultaneously operate an air pump, observe a light going off, and take a measurement on an air pressure meter. It also had the disadvantage of only measuring the pressure under a small blade-type connector. An improved device was made by Talley Medical Equipment Ltd., which provided a larger sensor with perforated metal sheet contacts. This allowed a maximum pressure to be identified under a larger area, reducing the number of readings which had to be taken. Talley further improved the device by eliminating the analog pressure gauge and replacing it with a digital display, thus making the reading easier. However, that unit still had the disadvantages of frequent sensor failures due to failures of the electrical contacts at the perforated metal sheets, and the user had to remember to turn off the power switch or the unit quickly ran down the batteries. A similar device was made by Next Generation and had the same faults. Diastron Ltd. uses a complex optical sensor which requires periodic recalibration.

Therefore, a need exists for a device having an improved sensor design which eliminates frequent failures, providing for more accurate readings and eliminating the problem of battery run-down when the user fails to turn off the device.

SUMMARY OF THE INVENTION

The present invention provides a device to satisfy the aforementioned need.

Accordingly, the present invention is directed to an interface pressure measurement device, comprising a sensor comprising two sensor sheets formed from thin flexible plastic material, each sensor sheet has a sensor area having flexible conductive ink printed thereon comprising a conductive surface with an electrical lead such that when the sensor sheets touch, an electrical contact is present forming a sensor switch, and the sensor also has sensor tubing. A digital device is connected to the sensor by the sensor tubing. The digital device comprises an enclosure, a push button, pressure transducer, signal conditioning means, microcontroller with processor means, analog-to-digital converter, memory means, clock, display, buzzer and battery/power supply wherein the processor means interrupts the battery/power supply current flow to shut off the digital device after a preset time. An inflator bulb having inflator tubing is connected to the digital device by the inflator tubing such that the inflator bulb is used to manually pump air through the digital device to the sensor whereby the pressure from the air in the sensor between the sensor sheets is sensed by the pressure transducer. When the microcontroller senses the opening of the sensor switch, the microcontroller through the processor means transmits a signal to the display to provide a visual indication corresponding to the pressure in the sensor and transmits a signal to the buzzer to provide an audible tone.

BRIEF DESCRIPTION OF THE DRAWINGS

Further features of the present invention will become apparent to those skilled in the art to which the present invention relates from reading the following specification with reference to the accompanying drawings in which.

DESCRIPTION OF THE PREFERRED EMBODIMENT

Figure 1:
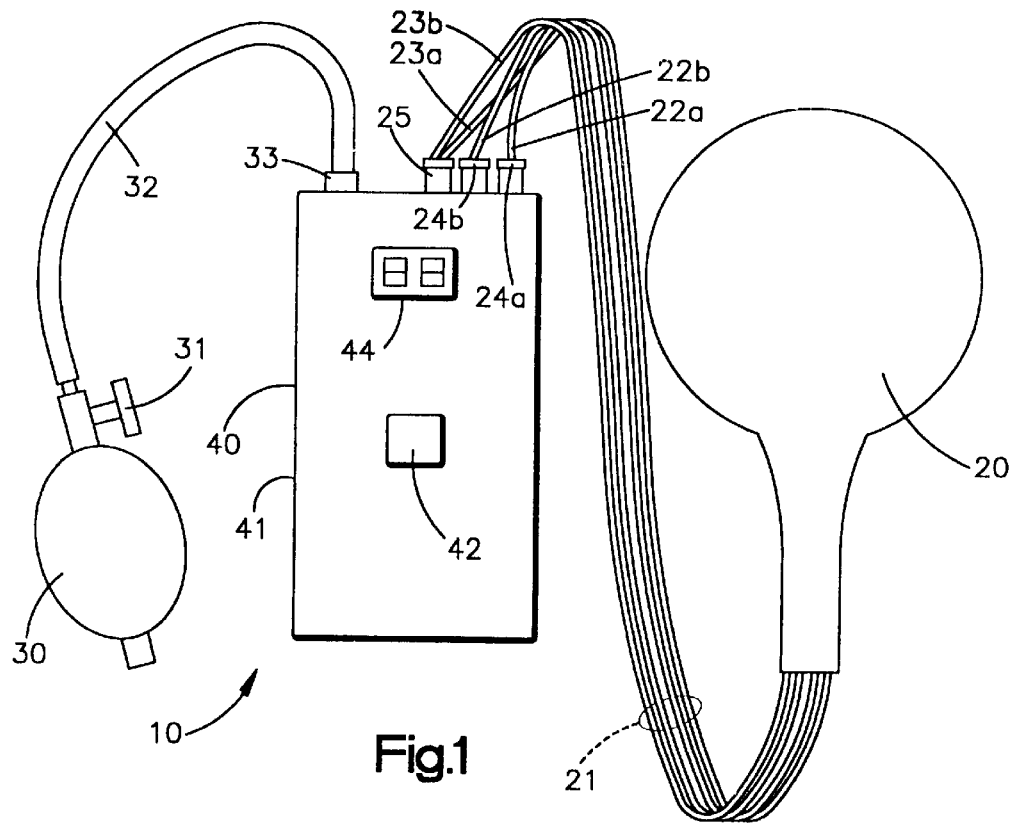
FIG. 1 is a plan view of the device of the present invention.
Figure 2:
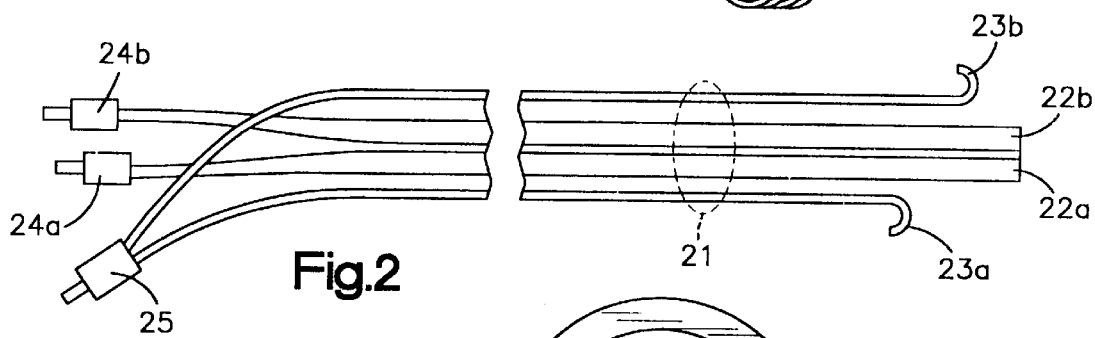
FIG. 2. is a detail of the sensor tubing.

Referring now to the drawings and, particularly FIG. 1 and FIG. 2, there is shown a plan view of the device of the present invention and a detail of the sensor tubing, respectively. The interface pressure measurement device 10 is composed of a sensor 20, inflator bulb 30, and digital device 40. The sensor 20 is connected to the digital device 40 by means of sensor tubing 21. The sensor tubing consists of two sensor tubes 22a and 22b and two sensor wires 23a and 23b. The two sensor tubes connect to the digital device enclosure 41 by means of tubing connectors 24a and 24b. The sensor wires 23a and 23b connect to the digital device enclosure 41 by means of an electrical connector 25. The sensor tubing 21 is preferably clear plastic tubing which can be made from polyvinyl chloride or any other material. The tubing connectors 24a and 24b are also typically made of plastic and provide an air-tight seal. The electrical connector 25 is preferably a mini phono jack. The tubing connectors 24a and 24b and the electrical connector 25 are detachable from the digital device enclosure 41 to allow easy replacement of the sensor 20. The device is turned on by pressing the pushbutton 42. The sensor 20 is placed in an appropriate location on or at the persons body. This can be in many locations depending upon the particular application and the pressure to be sensed. For example, the sensor 20 can be placed within a bandage wrapped around the person's extremity, between the person's buttocks and the seat of a chair in which the person is sitting, or between the body and a bed if the person should be reclining, to name just a few. The inflator bulb 30 is then manually pumped to pressurize the sensor 20. A push-button 42 starts the digital device 40 and allows the pressure readings to be displayed on the display 44. The push button 42, which is shown as a single button, may be replaced with any type of momentary switch.

The sensor 20 can be inflated by use of inflator bulb 30. The inflator bulb 30 is preferably of the same type that is used on a sphygmomanometer for reading blood pressures. As the inflator bulb 30 is manually pumped air flows, through the inflator bulb 30, through the inflator tubing 32, inflator connector 33, digital device 40, tubing connector 24a, sensor tubing 22a and into the sensor 20. The valve 31 can be turned to allow air to flow out of the sensor 20 through the reverse path.

Figure 3:
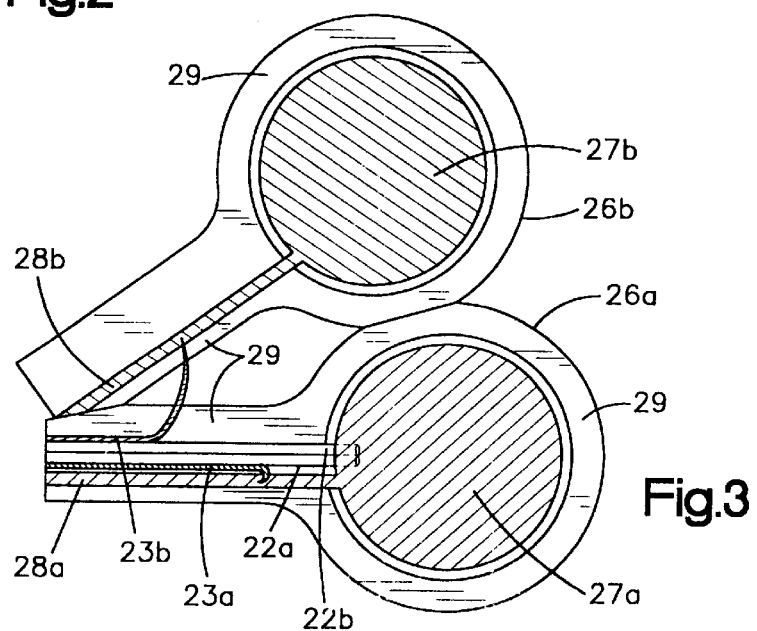
FIG. 3 is a view of the inside of the sensor with the sensor sheets splayed open.

Referring now to FIG. 3, there is shown a view of the inside of the sensor with the sensor sheets splayed open. The sensor 20 is made with two identical sensor sheets 26a and 26b of a thin flexible plastic material, such as vinyl. The two sensor sheets 26a and 26b are adhered together to form the sensor 20. The sensor sheets 26a and 26b each have a sensor areas 27a and 27b printed on them by using a flexible conductive ink which combined form sensor area 27. Preferably, this ink contains metal particles such as silver to conduct the electrical current. This is superior to the perforated metal sheet sensors used in the prior art in that it is thinner, more durable, and can be less expensive. Electrical leads 28a and 28b are also printed on each sensor sheet 26a and 26b using the same ink as the sensor area 27a and 27b. The sensor tubes 22a and 22b are placed alongside the electrical leads 28a and 28b and their ends extend into the sensor areas 27a and 27b. The ends of the sensor wires 23a and 23b are separated from the ends of the sensor tubing 22a and 22b and the end of the electrical insulation is removed so that the end of one sensor wire 23a can be electrically connected to the electrical lead 28a. This can be done with an electrically conductive adhesive or with the same sensor ink that is used to print the sensor areas 27a and 27b and the electrical leads 28a and 28b. The other sensor wire 23b is similarly connected to the electrical lead 28b on the second sensor sheet 26b which is placed face to face with the first sensor sheet 26a so that the two sensor areas 27a and 27b are touching one another. An adhesive 29 is placed as shown in FIG. 3 to allow the sensor sheets 26a and 26b to adhere to one another. Tape, not shown in FIG. 3, can optionally be placed over the ends of the sensor wires 23a and 23b to keep them from adhering to the adhesive on the opposite sensor sheet 26 during the manufacturing process. The two sensor sheets 26a and 26b are then pressed together to form a complete sensor. Sensing areas 27a and 27b act as a sensor switch 66 (not shown on FIG. 3). When the sensing areas 27a and 27b touch, an electrical contact is formed between sensor wires 23a and 23b and sensor switch 66 is closed. When air from the inflator bulb is forced into the sensor 20, separating the sensor areas 27a and 27b, sensor switch 66 is opened and there is no electrical contact between the sensor wires 23a and 23b. Pressure on the sensor 20 retards the opening of sensor switch 66 until the air pressure inside the sensor 20 exceeds the highest pressure point on the sensing areas 27a and 27b; at that point air is forced in-between the sensing areas 27a and 27b, thus opening the sensor switch 66.

Figure 4:
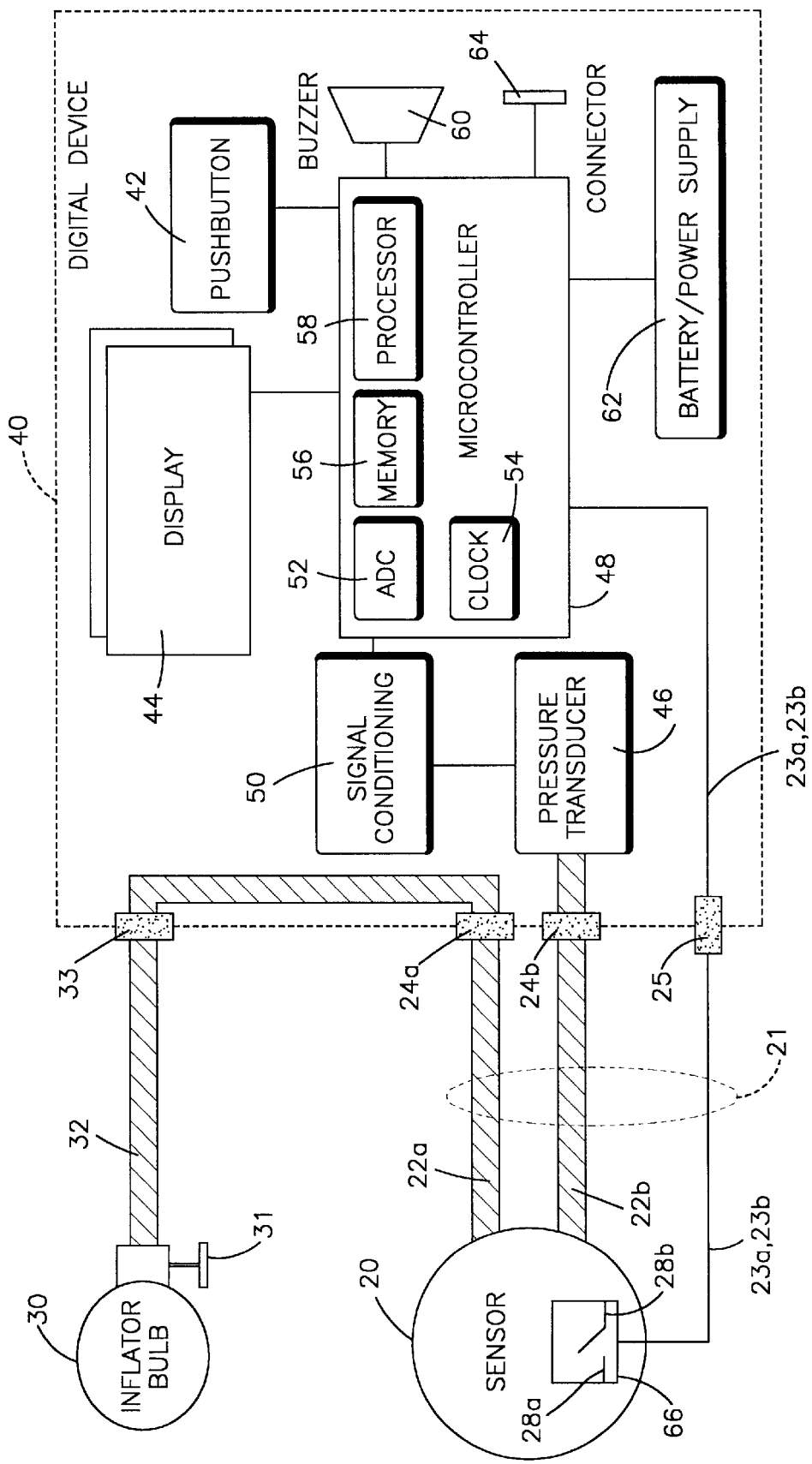
FIG. 4 is a block diagram of the device. The digital device 40 is enclosed in a digital device enclosure 41.

Referring now to FIG. 4, there is shown a block diagram of the device of the present invention. Air from the inflator bulb 30 flows through the inflator tubing 32 through the digital device 40, out through one of the sensor tubes 22a into the sensor 20. Sensing tube 22b connects the sensor 20 to a pressure transducer 46 located in the digital device 40. The pressure inside the sensor 20 is then sensed by a pressure transducer 46 which converts the sensed pressure to a corresponding millivolt signal in response thereto. It is important to have the pressure transducer 46 connected downstream of the sensor 20 (i.e.: after the sensor 20 so that the sensor 20 is located between the inflator bulb 30 and the pressure transducer 46), rather than upstream of the sensor 20 (i.e.: between the inflator bulb 30 and the sensor 20) so that the effects of the pressure transients from the inflator bulb 30 are minimized. The sensor wires 23a and 23b are connected to the electrical leads 28a and 28b, respectively, and the microcontroller 48. When the pressure exceeds the highest pressure point on the sensing area 27, the electrical contact is then broken, opening sensor switch 66 and there is no electrical continuity between sensing wires 23a and 23b. At this point, the microcontroller 48 senses the open sensor switch 66 and registers that the pressure in the sensor has just exceeded the pressure exerted on the sensing area 27. The analog-to-digital converter (ADC) 52 then reads the voltage of the millivolt signal from the pressure transducer 46 though signal conditioning means 50. The signal conditioning means 50 converts the millivolt signal from the pressure transducer 46 to a 0–5 volt analog signal to be read by the ADC 52. The signal conditioning means 50 is preferably an instrumentation amplifier built up with operational amplifiers. The ADC 52 converts the analog signal to a digital signal, typically at 8 bits of resolution. The microcontroller 48 can be any type of microprocessor that is preferably a microcontroller such as a 68HC11 made by Motorola. This allows the ADC 52, a clock 54, memory means 56, and processor means 58, all to be incorporated as one electronic component, in the microcontroller 48. However, they can be made from individual parts. The clock 54 keeps time for the microcontroller 48 and a pressure reading is recorded periodically, regardless of whether the sensor switch 66 is open or closed. These pressure readings are preferably taken at 50 KHz and low pass filtered at 500 Hz and the four readings around the opening of the sensor switch 66 are averaged. This allows a more consistent reading to be recorded. The memory means 56 contains calibration constants determined by the calibration of the pressure transducer 46 to relate the digital readings from the ADC 52 to an actual pressure, preferably recorded in mmHg. The processor means 58 reads the digital value from the ADC 52, performs the filtering described above, applies the calibration constants from the memory means 56, producing a reading in mmHg, and transmits a signal to the display 44 which provides a visual indication corresponding to the pressure in the sensor 20. The visual indication remains constant for a preset time to allow the user to easily read the display 44. The processor means 58 also sends a current to the buzzer 60, providing an audible tone for the user. Power for the system is provided by a battery/power supply 62. The microcontroller 48 can be programmed by a personal computer by means of the connector 64.

The display 44 is preferably a light emitting diode (LED) but can alternatively be a liquid crystal display (LCD) or any other type of display. Any number of digits may be displayed, however, interface pressures of greater than 99 mmHg are extremely high and must be treated to prevent decubitus ulcer formation. Two digits preferably give the greatest amount of information at the lowest cost.

After the sensor switch 66 is opened and a reading displayed, the processor means 58 turns off the power from the battery/power supply 62 after a pre-set time interval. Preferably, 10 seconds is used for this purpose. The processor means 58 can also be used to detect and send a signal to the display 44 to display error codes to provide the user additional information. The processor means 58 can detect low input voltages from the battery/power supply 62 and display a "E0" on the display 44. When the processor means 58 detects an open sensor switch 66 from the sensor 20 immediately after the push button 42 has been depressed an "E1" is displayed on the display 44 informing the user that the sensor is not connected, has not been deflated, or that there is a broken wire. When the processor means 58 detects that the sensor switch 66 has not been opened within 60 seconds of the push button 42 being actuated an "E2" is displayed on display 44 showing that the sensor has not been inflated within 60 seconds of the start of the push button 42 or that there is a defective sensor 20. The processor means 58 then turns off the power from the battery/power supply 62 after a preset time interval.

We claim:

1. An interface pressure measurement device for measuring the pressure applied upon a body, comprising:
   a) A sensor comprising two sensor sheets formed from thin flexible plastic material and said sensor having sensor tubing;
   b) A digital device connected to said sensor by said sensor tubing and further comprising an enclosure, a push button, pressure transducer, signal conditioning means, microcontroller with processor means, analog-to-digital converter, memory means, clock, display, and battery/power supply wherein said processor means interrupts said battery/power supply current flow to shut off said digital device after a preset time; and
   c) an inflator bulb having inflator tubing and connected to said digital device by said inflator tubing such that said inflator bulb is used to manually pump air through said digital device to said sensor whereby the pressure from the air in said sensor between said sensor sheets is sensed by said pressure transducer and whereby said microcontroller through said processor means transmits a signal to said display to provide a visual indication corresponding to the pressure in said sensor, said pressure transducer located downstream of said sensor such that the effects of the pressure transients from said inflator bulb are minimized.

2. The interface pressure measurement device of claim 1 wherein the shut off preset time of said digital device is 10 seconds or greater.

3. The interface pressure measurement device of claim 1, wherein said sensor sheets each has a sensor area having flexible conductive ink printed thereon comprising a conductive surface with an electrical lead such that when said sensor sheets touch, an electrical contact is present forming a sensor switch.

4. The interface pressure measurement device of claim 3 further comprising two sensor wires connected between said electrical leads and said microcontroller providing an electrical connection from said sensor switch to said microcontroller.

5. The interface pressure measurement device of claim 1 wherein said sensor sheets are formed from vinyl.

6. The interface pressure measurement device of claim 1 wherein said pressure transducer converts the pressure sensed to a millivolt signal and wherein said signal conditioning means converts said millivolt signal to an analog signal of about 0 to 5 volts.

7. The interface pressure measurement device of claim 6 wherein said analog-to-digital converter reads said analog signal from said signal conditioning means and converts it to a digital signal.

8. The interface pressure measurement device of claim 1 wherein said clock keeps time for said microcontroller and causes a pressure reading to be recorded periodically.

9. The interface pressure measurement device of claim 1 wherein said memory means contains calibration constants determined by the calibration of said pressure transducer to relate the digital signal from the analog-to-digital converter to actual pressure.

10. The interface pressure measurement device of claim 1 wherein said display is a light emitting diode.

11. The interface pressure measurement device of claim 1 wherein said display is a liquid crystal display.

12. An interface pressure measurement device for measuring the pressure applied upon a body, comprising:
    a) A sensor comprising two sensor sheets formed from thin flexible plastic material wherein said sensor sheets each has a sensor area having flexible conductive ink printed thereon comprising a conductive surface with an electrical lead such that when said sensor sheets touch, an electrical contact is present forming a sensor switch, and said sensor having sensor tubing;
    b) A digital device connected to said sensor by said sensor tubing and further comprising an enclosure, a push button, pressure transducer, signal conditioning means, microcontroller with processor means, analog-to-digital converter, memory means, clock, display, and battery/power supply; and
    c) An inflator bulb having inflator tubing and connected to said digital device by said inflator tubing such that said inflator bulb is used to manually pump air through said digital device to said sensor whereby the pressure from the air in said sensor between said sensor sheets is sensed by said pressure transducer such that when the microcontroller senses the opening of sensor switch such that said microcontroller through said processor means transmits a signal to said display to provide a visual indication corresponding to the pressure in said sensor, said pressure transducer located downstream of said sensor such that effects of the pressure transients from said inflator bulb are minimized.

13. The interface pressure measurement device of claim 12 wherein said processor means interrupts said battery/power supply current flow to shut off said digital device after a preset time.

14. The interface pressure measurement device of claim 12 wherein said digital device further comprises a buzzer and said processor means transmits a signal to said buzzer to provide an audible tone upon the opening of said sensor switch.

15. The interface pressure measurement device of claim 12 wherein said digital device includes a single push button.

\* \* \* \* \*